United States Patent [19]

Place et al.

[11] Patent Number: 4,652,354
[45] Date of Patent: Mar. 24, 1987

[54] PROCESS FOR MOULDING GELS USABLE FOR THIN LAYERS ELECTROPHORESIS AND USE THEREOF

[75] Inventors: John F. Place, Geneva; André Bregnard, Le Lignon, both of Switzerland

[73] Assignee: Battelle Memorial Institute, Geneva, Switzerland

[21] Appl. No.: 656,462

[22] Filed: Oct. 1, 1984

[30] Foreign Application Priority Data

Oct. 4, 1983 [CH] Switzerland .......................... 5390/83

[51] Int. Cl.$^4$ ............................................. G01N 27/26
[52] U.S. Cl. .................................................. 204/182.8
[58] Field of Search ..................... 204/299 R, 182.8; 264/311, 40.7; 425/147, 140

[56] References Cited

U.S. PATENT DOCUMENTS

| | | | |
|---|---|---|---|
| 4,035,377 | 7/1977 | Detroy | 204/299 R |
| 4,169,036 | 9/1979 | Anderson et al. | 204/299 R |
| 4,325,897 | 4/1982 | Zerle et al. | 425/140 X |
| 4,338,071 | 7/1982 | Daubenbuchel et al. | 425/147 X |
| 4,362,685 | 12/1982 | Simioni | 264/311 X |
| 4,416,841 | 11/1983 | Corea et al. | 264/311 X |
| 4,422,984 | 12/1983 | Neefe | 264/311 X |
| 4,431,506 | 2/1984 | Gorman, Jr. et al. | 204/182.8 X |
| 4,440,699 | 4/1984 | Smid et al. | 425/140 X |
| 4,517,145 | 5/1985 | Knopf | 425/140 X |
| 4,533,307 | 8/1985 | Ansorge | 204/299 R X |
| 4,534,916 | 8/1985 | Wichterle | 264/311 X |

Primary Examiner—Terryence Chapman
Attorney, Agent, or Firm—Cushman, Darby & Cushman

[57] ABSTRACT

A mould for the moulding by casting of thin, crosslinked, polymerized resin films is used which is subjected, when being filled with the liquid to be polymerized, to a centrifugal force field exceeding that of the earth gravitation field, the whole being for equalizing the intimate structure of the polymer and to expel therefrom the bubbles of gas possibly present therein.

11 Claims, 7 Drawing Figures

PROCESS FOR MOULDING GELS USABLE FOR THIN LAYERS ELECTROPHORESIS AND USE THEREOF

The present invention has as its object a process for moulding gels usable for thin layer electrophoresis and other related techniques.

It is known that the techniques of electrophoresis called also sometimes electrochromatography consist of subjecting to an electric field provided by two electrodes, one anode and one cathode, an electroconductive solution of positively or negatively ionised molecules so as to cause the migration of the latter in direction of the electrode having a sign opposite to that of the charge of said molecules. The rate of electromigration of the charged molecules is determined by some of their physical chemical parameters, namely their mass, their charge, and the diffusion constant in the medium under consideration which enables to effect the separation of the various chemical species as a function of parametric values specific to these various species. One therefore obtains, at the end of the operation, a chromatogram or electropherogram wherein, after development, the various species of molecules thus separated appear under the form of points or spots or successive areas more or less diffuse depending of the efficacy of the separation.

This efficiency of the separating capacity is connected among others to the temperature of the electrophoretic medium because the higher the temperature, the greater the effects of thermal convection, as well as the random movement of the molecules (diffusion) and the less sharp the electrophoregram. Besides, it is evident that such defects increase in proportion to the duration of the electrophoresis, the time necessary to effect, by means of the latter, an effective separation of the species to be identified being naturally a function of their relative displacement rates in the electric field. Therefore, in order to minimise as much as possible the aforementioned shortcomings and also for evident practical reasons, it is necessary that the duration of the electrophoresis be as short as possible while being long enough to ensure that the various sepcies to be identified are sufficiently separated from each other to be distinguished. It will therefore be advantageous to increase as much as possible the migration velocity of the components under analysis but preferably without raising the temperature.

Now, a charged particle (q) which moves in an electroconductive liquid under the influence of an electric field of magnitude H displaces itself at a rate v determined by the existence of two oppositely acting forces of equal value: a first force qH acting in the direction of the displacement and a second force $KTv/D$ due to the friction of the particle on the medium and thus acting in an opposite direction (K is the Bolzmann constant; T is the absolute temperature and D is the diffusion constant, a parameter specific to the molecule under discussion). Thus, if T is maintained constant, it is possible to increase v by increasing H. Now, in such a medium, H is defined by the following relation $H=i\gamma A$ where i is the intensity of the current in the electrolysis medium, $\gamma$ is the conductance and A is the cross-section of the electrophoretic medium. As a consequence, for increasing H without increasing T (that is to say without increasing the energy dissipation by an increase of the current i), one will have to act by decreasing the thickness of the electrophoretic medium.

Under usual practice for separating organic molecules such as proteins or nucleic acids, it is possible to use electrophoretic media constituted by gels (agarose, starch, polyacrylamide, etc.) more or less cross-linked according to the needs. Such gels have the property of decreasing the convection displacements in the electrophoretic liquid and to improve the fractionation of the molecules to be separated as a function of their size and their bulk relative to the mesh size of the network constituted by the gel as well as with regard to their surface affinity properties relative to the molecules of the latter.

By reasons of considerations discussed above, one has attempted lately to prepare electrophoretic gels in the form of films as thin as possible (of the order of 20 to 500 $\mu$m), the using of such thin films presenting the following advantages: to decrease the heating effect due to the Joule effect with the possibility of applying larger electric fields allowing for a better fractionation resolution within shorter analytical periods. Better dissipation of the heat produced with, as a consequence, a smaller temperature gradient through the gel thickness and a decrease of the effects which depend on the thermal convection movements in the medium. Also, improved sensitivity is obtained by reason of the reduction of the total amount of sample required for the analysis.

Many publications have issued recently in this field among which one can cite the following: W. ANSORGE et al, J. Chromatograhy 202 (1980), 45–53; P. G. RIGHETTI, Electrophoresis '81 (1981), De GRUYTER & CO, Berlin-New-York, p. 2–16 et 182–188; J. W. JORGENSON et al, Clin. Chem. 27 (1981) 1551–1553; H. R. MAURER et al, Analyt. Biochem 46 (1972), 19–32; V. ANSELSTETTER, J. Chromatography 172 (1979), 49–56; C. J. Van OSS, Methods Immunodiagnosis (1973), 175–194; A. GOERG et al, Analyt. Biochem 89 (1978), 60–70; A. GOERG t al, J. Biochemical and Biophysical Methods 3 (1980), 273–84.

According to the afore-mentioned references, the techniques used for preparing thin layer gels comprise the following embodiments 1. one constructs a mould by means of two rigid plates (made of glass for instance) fitted to each other by cross-bars (one base cross-bar and two side-cross-bars) and one fills this mould placed vertically by intoducing therein, by means of a filling device, the solution of monomers whose subsequent polymerization provides the gel sought after;

2. according to a different technique one applies the monomer solution over a plate provided with cross-bars on three of its sides and held horizontally, then one applies a second plate on the first one, both plates being maintained in a parallel orientation to each other by the cross-bars so as to eliminate the excess of the liquid caught in-between, this excess being driven off and escaping through the opening which results on one side of the mould, from the absence of a fourth cross-bar.

3. according to a technique resembling the previous one after depositing the solution on a first plate, one progressively slides the second plate over the first one so as to push off, in the direction of the opening of the mould by a scraping effect, the air bubbles possibly trapped in the liquid.

However, these techniques have certain drawbacks and particularly the following: when one fills a mould held in a vertical position by pouring the liquid into it, it is practically impossible to completely eliminate the possible imperfections due to local density variations and to the air bubbles, the presence of which modifies the polymerisation conditions and disturbs the migration of the proteins subsequently subjected to the electrophoretic process. In contrast, the technique (3) mentioned above, although it is very efficient to eliminate such defects, is lengthy, costly to be implemented and requires a great operating skill.

Besides, the defects of homogeneity of the thin layer gels can amplify some drawbacks in connection with the bringing about of the electrophoresis operation such as losses of water in the gel, some preferential displacement of the samples to be analysed in the surface portions of the gel and thermal convection effects in imperfectly cross-linked areas of the medium.

The process of the invention, such as disclosed in claim 1, remedies these drawbacks. For implementing this process, one uses a mould formed by two rigid plates maintained substantially parallel one to the other at a distance of about 5 to 500 μm, for instance by means of cross-bars as in the previous art. The opening of the mould located at the edge of the mould or at close proximity thereto, is arranged in a manner such that when a liquid is introduced therein, the latter flows along the inside surface of the parallel faces, this being like in the case of the prior art moulds which are placed, when being filled, in a vertical position.

In order to prepare the gel according to the process of the invention, one fills the mould with a liquid composition or an electroconductive solution of one or more substances, for instance monomers or prepolymers susceptible to set or to harden into a mass and thus to provide a gel. One allows the gas or air bubbles or other local inhomogeneities possibly present in the liquid of the mould of the mould to be eliminated by debubbling or resorption (i.e. dissolution in the liquid) then, when the fluid becomes homogeneous, one causes it to harden by the usual means; catalytic polymerization or otherwise, or cooling in the case when a hot gelatin solution is involved, and others, so as to obtain a gel. The particular feature which characterizes this process relatively to the prior art is the fact that one operates under the influence of an artificial gravitational field, this field being caused by the rotation of the mould and the forces therefore provided being directed so that the filling liquid is driven from the opening of the mould towards the bottom of this mould. Therefore, this gravitational field is applied to the mould exactly like the terrestrial field in the case of a mould to be filled vertically, the difference provided by the invention being, in connection with the intensity of this field due to the rotation of the mould. This intensity of the field can attain several g, for instance 5 to 200 g's, or more if desired.

The use of a gravitational field of intensity over that of the terrestrial field for filling moulds intended for moulding thin films for electrophoresis presents the main advantage to provide a very fast and complete elimination of local inhomogeneity defects and other air bubbles which are possibly present in the liquid to be polymerised. This effect, per se, is not new because it is known to degas liquids by centrifugation (see for instance, Chem. Ing. Tech 44 (1972), 497–503 49 (1977), 747; Japanese patent application Kokai No. 80 135, 618); however, it does not seem that such a technique has ever been proposed for the moulding of thin layer gels for electrophoresis applications or for other related techniques (thin layer chromatography, isoelectric focusing, etc.)

Another advantage of moulding such gels under the influence of a centrifugal force is to enable in some cases to achieve a property gradient after polymerization. Indeed, under the influence of a force that varies radially in proportion to the distance from the centre to the periphery ($F_c = V^2/r = \omega^2 r$), a solution of monomer not yet polymerized or being polymerized subjected to a rotation effect can, if the angular velocity is sufficient, densify at the periphery and rarefy at the centre. If a complete polymerization takes place during rotation the variable density gradient will be maintained in the terminated gel; such a technique enables thus obtaining thin layer gels with variable properties according to a given function, this being with solutions which are normally homogeneous at the start. It will be noted in this connection that for obtaining property gradient gels according to usual techniques, one proceeds by simultaneously introducing into the mould two monomer solutions with different concentrations, the ratio of the addition rate for the two components being varied in the course of time according to a given relationship. The process of the invention enables thus to obtain such gels in a much simpler and better controlled manner than with the older techniques. The invention is also suitable for the preparation of composite gels by the successive additions of solutions of different natures or concentrations, the various corresponding portions of liquid being efficiently maintained at their respective positions by the centrifugal force so that they cannot mix together during the filling of the mould or when the subsequent polymerization is carried out.

The gels which can be prepared according to the invention are of various natures and comprise practically all cross-linked polymers generally usable in this field. Among the latter, one can cite the gels of gelatine, aragose, starch, polyacrylamide and others. In the case of gelatin solution, one casts the latter under heat and the hardening takes place afterwards by cooling. Regarding the polymerization of the monomers, this can be effected according to usual means, for instance by incorporation into the solution before moulding of initiators or activators of polymerization normally required for polymerization at the considered temperature, the mould being or not maintained under rotation after debubbling until the end of polymerization. One can find indications on these types of gels and the means for polymerizing them in the above-mentioned references. Although as has been shown above, it can be interesting to proceed with the polymerization under the influence of a centrifugal force, this is not necessary in the cases when the centrifugation is only intended to improve the intrinsic quality of the gel material (homogeneous gels without air bubbles); in such a case, one can, after the debubbling step, stop the rotation of the mould and allow the polymerization to proceed under rest.

In contrast, one can effect the polymerization of a solution or mixture of photopolymerisable monomers by incorporating to the mixture one or several appropriate photoinitiators. Once the mould is filled and the solution is debubbled by centrifugation, one proceeds to the hardening of the latter by irradiation by means of a convenient actinic source, this operation being carried out as well on standing as under rotation. In the latter case, each zone of the mould regularly passes, in turn, in facing relationship with the irradiation source with the result that the exposure of the solution to be polymerized is particularly regular and the gel which results therefrom is very homogeneous.

BRIEF DESCRIPTION OF THE DRAWINGS

For the description that follows, one will refer to the annexed drawing that represents two devices for embodying the invention and one variant.

Figure 1:
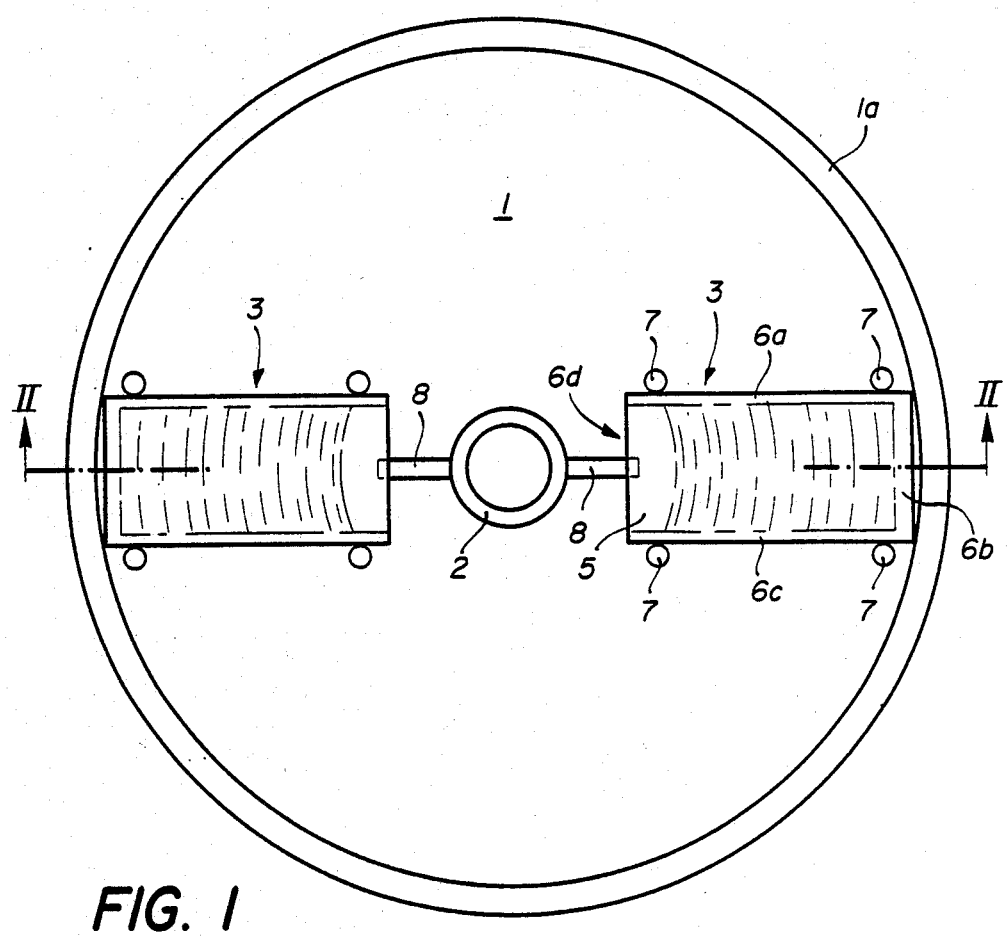
FIG. 1 represents in plan view the essential parts of a device enabling to introduce a solution into a mould and its debubbling by centrifugation.

The device represented in FIG. 1 comprises the main following elements: a circular plate 1 mounted on a hollow shaft 2, this plate being used to support one or several moulds 3 intended for moulding thin polymer films in the form of gels. Each of the moulds 3 comports a lower rigid plate 4 and an upper rigid plate 5 (made of glass or of plastic) these plates being maintained approximately parallel by assembly means constituted by cross-bars 6a, 6b and 6c. The moulds 3 are maintained on the plate on one hand by a shoulder 1a of the latter and on the other hand by detachable studs 7 made of plastic whose removal enables to withdraw the moulds after their filling with a liquid and possible subsequent polymerization of this liquid. The hollow part of the shaft 2 communicates with the entrance 6d of the moulds by a flexible capillary duct 8 whose external end is flush with opening 6d or penetrates very slightly therein.

Plate 1 is rotatively mounted on a frame not represented and driven by a motor also not represented.

Figure 2:
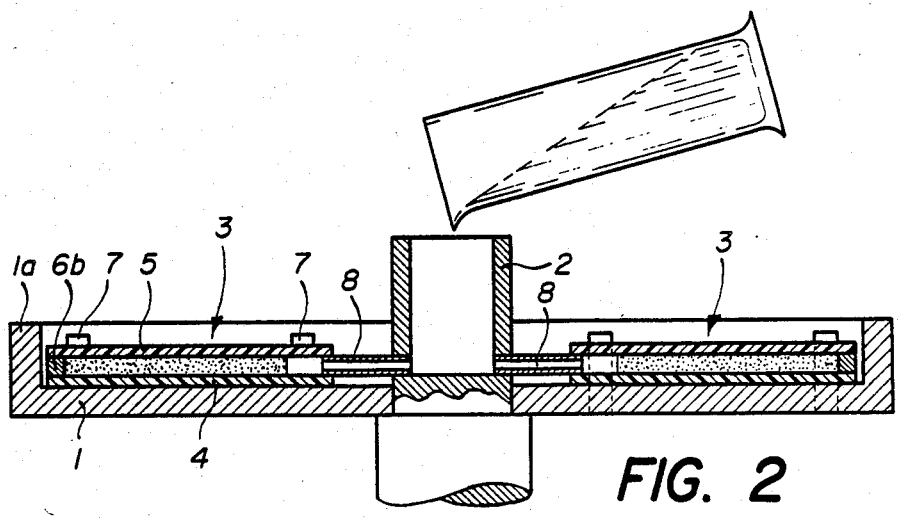
FIG. 2 represents a cross-section of said device according to the line II—II of FIG. 1.

For filling one or several moulds, one puts this mould or these moulds on the plate and one maintains them firmly horizontally by means of studs 7. Naturally, the plate can be made to freely rotate and can be balanced either by the presence of the second mould (as shown in the drawing) of by an appropriate counterweight. After checking that the output ends of duct 8 are well in communication with the opening 6d of the mould, one starts to rotate the assembly and one introduces the solution intended to provide the gel in the hollow upper part of the axis 2 as schematically shown in FIG. 2. The liquid penetrates by means of tube 8 into the mould 3, and under the action of the centrifugal force it accumulates to the bottom of the latter while the air bubbles and other defects possibly present in the liquid are rapidly expelled by reason of the existence of the gravitation field markedly exceeding that of gravity. Naturally, the rate of rotation of the rotatable assembly depends on the working conditions, the nature of the solution, the viscosity, the flow parameters and others and will be determined by the specialist as a function of these factors and of the operating means. The solution to be polymerized (for instance an aqueous 5% solution of acrylamide containing as cross-linking agent, for instance 1-2% of methylen-bis-acrylamide) can contain either a radical polymerization initiator, for instance a peroxide, or a photoinitiator (for instance riboflavin or any other appropriate photoinitiator). In the first case, once the mould is filled, it is maintained under rotation (for instance at reduced speed) the time required for the liquid to harden into a mass and become unable to escape through the mould opening when the movement of the latter is stopped. In the second case, one fixes above the device under rotation an actinic source (for instance a mercury vapor lamp providing 40 w/dm$^2$ at 15 cm) and one proceeds to the irradiation of the moving mould, this irradiation being from a few seconds to a few minutes depending on the liquid composition.

Once the liquid is polymerized, one stops the rotating device and one uses the film of gel in an analytical operation or an electrophoretic preparation according to usual means.

Figure 3:
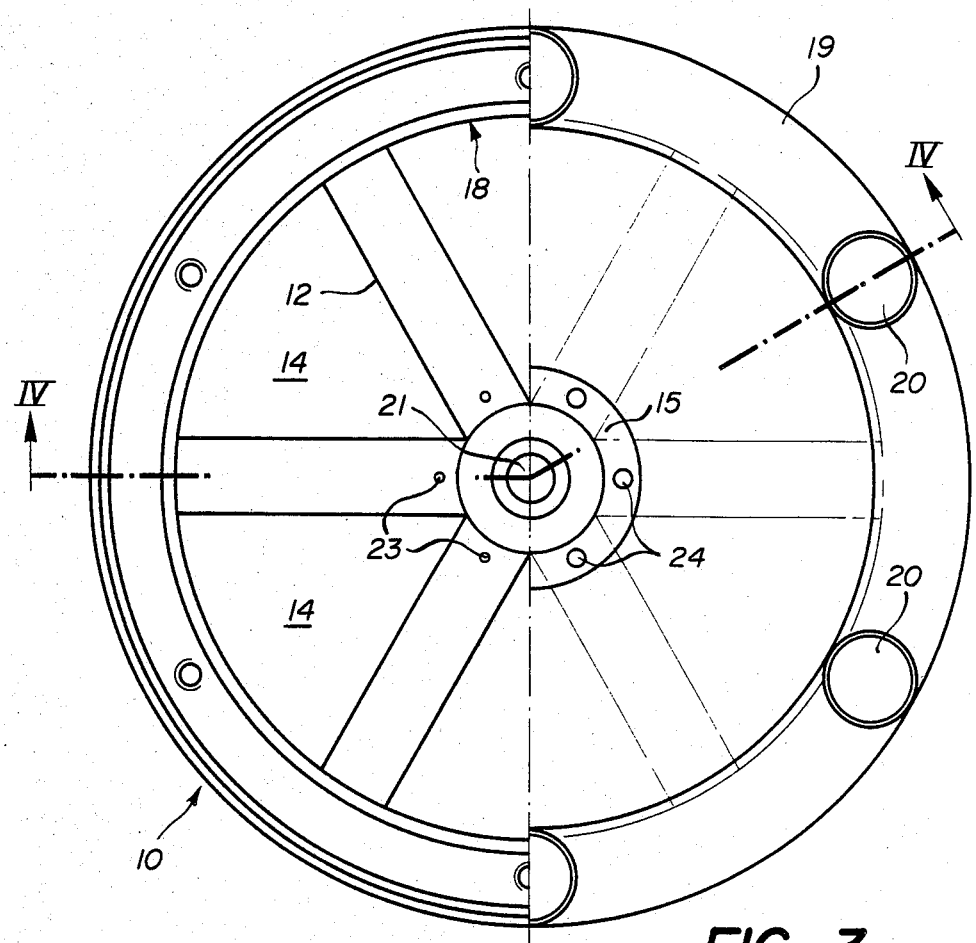
FIG. 3 is a plan representation with partial sections of a mould and of a device enabling to fill this mould with a liquid by centrifugation.
Figure 4:
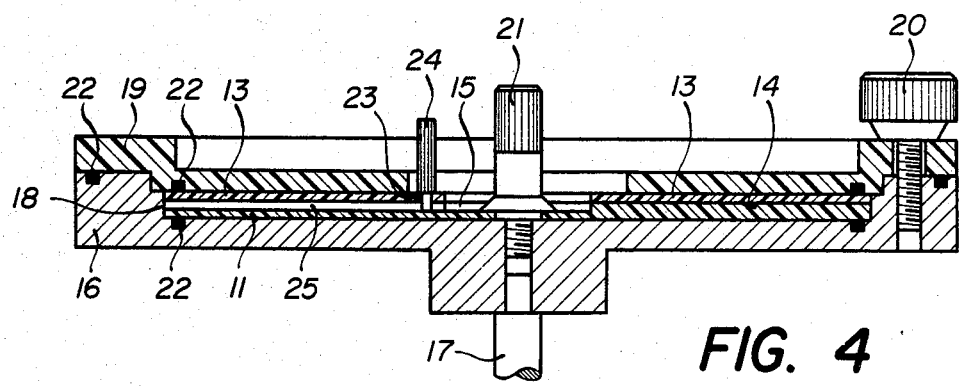
FIG. 4 represents a vertical section of the device of FIG. 3 according to line IV—IV or FIG. 3.

The device represented on FIGS. 3 and 4 comprises a mould 10 constituted by a lower disc 11, pierced at its centre, in which are machined radial recesses 12, and a second disc 13 also pierced at the centre adjusted concentrically on the upper face of disc 11. Recesses 12 constitute the inside volume of the mould which comprises as shown on the drawing, six independent compartments 12. These compartments are delineated on one hand by the bottom of recesses 12 and the portions of the disc 13 which cover these recesses, these surfaces contituting the main faces of the mould, and on the other hand, by the side-walls of sectors 14 of the disc 11 (sectors which constitute the means for assembling and maintaining in an abutting position the main faces of the mould) whose level with regard to the bottom of recesses 12 determines the thickness of the inside volume of the mould and consequently that of the desired films of gel. The edges of these sectors 14 constitute, in the case of each compartment, two of the secondary faces of the mould.

The diameter of the central hole of disc 13 is smaller than that of the corresponding hole of disc 11 so as to provide, by interrupting the abutting and assembling means of the main faces, annular opening 15 for filling the various compartments of the mould.

The present device further comprises a lower circular plate 16 mounted on a rotation axis 17 and comporting a shoulder 18 whose height approximately corresponds to the thickness of the mould, the latter fitting into the recess comprised between the bottom of plate 16 and said shoulder 18; the edge of the latter constitutes then the third secondary face which limits the volume of the mould 10.

The present device further comprises a circular lid 19 which can be affixed to plate 16 by knurled knobs 20 and a central bolt 21 enabling to make integral together the mould 10 and the plate 16. The tightness to liquids of the various organs thus put together is ensured by a series of O-ring joints 22. Finally, the device further comprises, pierced in a circular central zone of disc 13, holes 23 the crosssection of which can take any shape (circular, square, rectangular or others) in which one can engage elements in form of removable pegs 24 whose lower part, which presents a section corresponding naturally to the inside dimension of holes 23, rests against the inside face of the disc 11. The purpose will be seen later of these elements 24 whose shape and cross-section can be any provided their lower part matches with the shape of holes 23, that they can be easily introduced therein and that they can be extracted manually therefrom. p In order to implement the process of the invention by means of the present device, one preferably proceeds as follows: at the beginning of the operation, the main elements, mould, plate and lid are taken apart and the discs 11 and 13 (generally made of glass or of a plastic transparent to actinic rays) are carefully washed, rinsed with distilled water and dried. These various parts are thereafter reassembled and the assembling elements correctly tightened and locked by means of bolt 21 and knobs 20. One thereafter introduces into their respective recess the pegs 24 and one starts rotating the device by means of the motor not represented. When the desired angular velocity is reached and the centrifugal force field is achieved, one introduces, for instance by means of a syringe whose tip is directed through the opening 15, a solution whose polymerization will provide a gel. The addition is continued until the level of the liquid (indicated by FIG. 25) is flush with the annular edge of disc 13 (or at least when it passes the position of holes 23). After a waiting period provided to allow for debubbling and homogeneising, one then proceeds to the polymerization of the liquid as indicated with regard to the first embodiment, the lid 19 being made of a transparent plastic, for instance a lucite UV and when the liquid has solidified into a gel, one withdraws pegs 24, the removal of the latter providing, in the mass of gel, holes or recesses usable subsequently for the introduction into the gel of the samples to be subjected to electrophoresis. It can be thus easily understood that these recesses can be of any shape according to the needs, the sample size and the shape of the electropherogram which one desires to obtain. Thus these recesses can have a square, circular or oblong shape, for instance an arc of a circle extending the full width of compartment 12. As a variation, one can have several holes or wells side by side by providing a number of holes 23 and elements 24 exceeding 1 per compartment.

It should be remarked that the present embodiment enables to easily achieve gels with two or several superimposed sections by providing, when filling the mould, a successive addition of two or several solutions. In particular, one commonly uses a technique in which one provides near the centre of the rotation a thin portion of a particular gel (stacking gel) which enables an appropriate preliminary grouping of the components of the sample to be analyzed before the latter can penetrate in the main portion of the gel film. Thus, for instance, the stacking gel has the property to allow the spreading of a sample, having first been added at only one point over the entire width of compartment 12. To achieve such a gel film, one successively uses two filling solutions; the first one accumulates from the periphery of the mould to the $\frac{7}{8}$, for instance, of the total capacity thereof and the second one enables to achieve a central annular portion concerns the remaining $\frac{1}{8}$ of the mould area. It should be remarked that, according to one particular technique, one can add, as the terminal filling portion, a solution (also hardenable subsequently when the gel is formed) containing precisely, in addition, the sample to be subjected to electrophotoresis. The advantage of this modification resides in providing a perfectly regular distribution of the sample over the main body of the gel in which the electrophotoresis is to be carried out.

Figure 6:
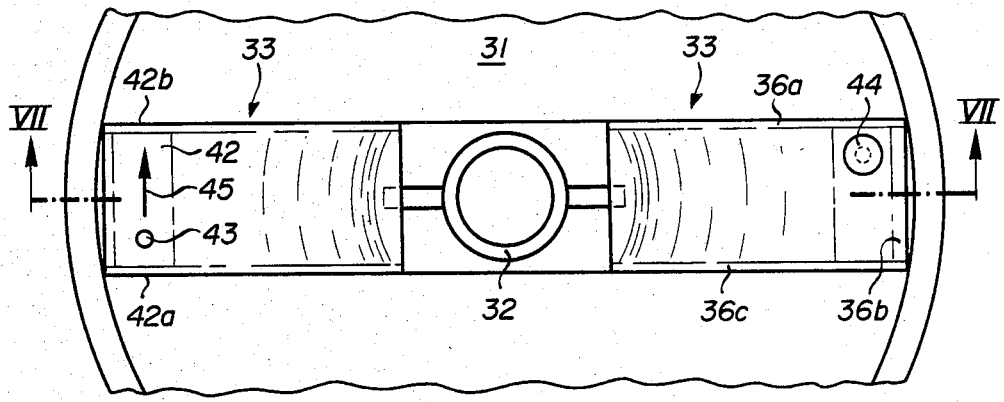
FIGS. 6 and 7 illustrate a variant of the embodiment of FIGS. 1 and 2.
Figure 7:
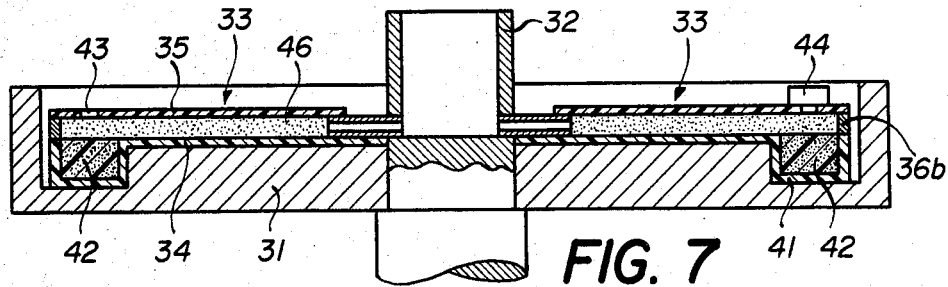

The variant represented in FIGS. 6 and 7 comprises generally the same elements as the device illustrated on FIGS. 1 and 2, namely the plate 31, a hollow shaft 32 and moulds 33. These moulds are constituted by a lower plate 34 and an upper plate 35 assembled by cross-bars 36a, 36b, and 36c. The lower plate 34 is not flat on the whole surface thereof like in the device of FIGS. 1 and 2 but presents in the vicinity of the periphery a U-shaped configuration 41 so as to provide at the bottom of the mould a recess or groove 42 of any depth, this depth being of the same order of magnitude as, or exceeding, the thickness of the mould such as illustrated on the drawing by the distance between plates 33 and 34. Further to the afore-mentioned elements, the present variant also comprises means identical to that already disclosed with regard to the embodiment of FIGS. 1 and 2 are, namely lateral tubes 38 for filling the mould and locking elements not represented. Besides, the upper plate 33 comprises openings 43 which can be plugged with plugs 44.

For casting a film according to the invention by means of the above-mentioned modification, one proceeds identically as previously disclosed with however the following additional phases: one starts by assembling on plate 31 the lower plate 34 provided with the assembly cross-bars 36a, 36b, and 36c, the part designated by 41 fitting into an appriate groove of the plate 31. One fills the groove 42 by usual means with a first composition providing a first gel whose quantity is such that its upper level is flush with the inside surface of the main part of plate 34. One causes thereafter the setting of the first composition, one puts into place the upper plate 35 and one injects a sample to be analysed by electrophoresis through opening 43 so that it comes into contact with the first gel in the vicinity of one of its ends 42a as indicated on the drawing. Once the sample has been incorporated into the first gel, one withdraws the mould and after having contacted the ends 42a and 42b of the gel with electrodes suited for performing an electrophoresis analysis according to ussual means, one carries out this electrophoresis for a time required for separating the sample into its various components, the latter migrating sidewise relative to the mould as indicated by the arrow 45. Once this first electrophoretic separation is completed, the removed components are reassembled on plate 31 and the forming of a second gel in area 46 is carried out exactly as in the embodiment illustrated previously with reference to FIGS. 1 and 2. Once this second gel has hardened, it is electrolytically in contact with the first gel and it is therefore possible by subjecting this second gel to a new electrophoresis operation according to usual means but oriented at right angle relative to the arrow 45 to provide a new separation in a longitudinal direction of each of the components which were individualized in the first electrophoresis. Such operation is known per-se (two-dimensional electrophoresis) and does not belong to the invention. In contrast, the present invention is suitable according to the present variant for preparing in a very simple manner a thin layer gel for electrophoresis whose migration starting zone for the sample contains the latter distributed in fractionated form over the whole width of this zone, this fractionation resulting from a first electrophoretic operation directed at right angle (or according to any angle preferably near 90°) relatively to that of said electrophoresis.

The following examples illustrate the invention

EXAMPLE 1

A device such as that represented on FIGS. 3 and 4 was used which presented the following significant parameters: diameter of the mould 20 cm; thickness 0.1 mm; rotation velocity variable between zero and 3000 r.p.m.; filling liquid: acrylamide solution at 5% with a density about 1.

Before undertaking a practical test of debubbling according to the process of the invention, the radial centripetal ascending force was calculated to which the air bubbles enclosed in the filling liquid in the mould are subjected as a function of their distance from the rotation centre and their depth of immersion in the liquid. It will be understood that the term of ascending force is used for designate the force to which the bubbles are subjected by virtue of the corresponding volume of displaced liquid, although this force is directed actually horizontally. For this calculation, the following basic elements have been used for the understanding of which reference is made to FIG. 5: on the graph of FIG. 5 have been indicated in cm, on one hand the distance (x) from the rotation axis at which the air bubble trapped in a rotating liquid is located as well as the depth (h) at which it is placed relative to the upper level of this liquid whose total depth is 7 cm, and on the other hand, (y axis) the centripetal force oppposing the gravitation field to which it is subjected. These values have been indicated for rotation velocities of 300, 600, 900 and 1200 r.p.m. respectively.

The other data of the calculation are the following:
T (absolute temperate) = 300° K.
n (number of moles of gas) = $10^{-6}$
R (gas constant) = 8.317 $kgm^2/sec^2$.mol. °K.
At (external pressure) = 100130 $kg/m.sec^2$
$\rho\rho$ (density of the liquid) = 1000 $kg/m^3$
h (height of the liquid) = 0; 0.03; 0.7 m
x (rotation radius) = 0.03, 0.06, 0.1 m
$a_c$ (centripetal accelaration) = $\omega^2 \times m/sec^2$
$\omega$ (rotation velocity) = $2\pi/t$ radians/sec
t (time of one revolution) = 60 $(rpm)^{-1}$
M (average molecular mass of air) = 28.56

In the following table, the following data are indicated as a function of the rotation frequency (rpm) and of the distance from the centre (x), the ascending forces in Newtons $\times 10^{-6}$ and, within parenthesis, the centripetal acceleration (in multiples of g, the acceleration of gravity) to which the bubbles placed at such distances are subjected, these last values being obtained from the following relation $[(2\pi \cdot rpm/60)^2 \cdot x]/9.81$.

Ascending force and (acceleration) for x = (m)

| rpm | 0.03 | 0.06 | 0.1 |
|---|---|---|---|
| 300 | 737 (3) | 1448 (6) | 2298 (10) |
| 600 | 2947 (12) | 5506 (21) | 7696 (40.2) |
| 900 | — (27.2) | — (54.3) | — (90.5) |
| 1200 | 11790 (48.3) | 18360 (96.6) | 18860 (160) |

Figure 5:
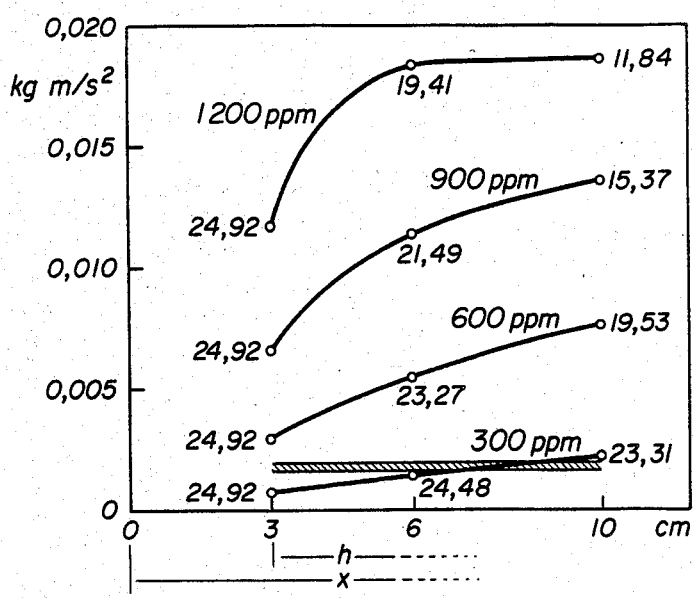
FIG. 5 is a graph for illustrating the relation which exists between the position of a gas bubble immersed at various depths in a liquid subjected to a centrifugal force and the escaping force to which this bubble is subjected.

The ascending forces indicated in FIG. 5 are calculated by taking account of the volume of the bubble immersed in the liquid under rotation and of the hydrostatic force which it generates by reason of the corresponding volume of liquid displaced minus the centrifugal force. The following relation is used:

$$\text{Ascending force } (N) = \left( \frac{nRT}{At + \rho h a_c} \right) \cdot \rho a_c - nMa_c$$

In FIG. 5, the four groups of three values of the aforementioned ascending forces (as a function of the rotation frequency) were plotted vertically on the y axis calibrated in N (or kg.m/sec) then these groups of points were approximately connected together to provide a curve showing the relative variation of these forces as a function of the rotation frequency and of the distance from the centre. It can be seen on the graph that the resulting effect which is relatively progressive at low velocities is significant for higher velocities particularly near the rotation centre and becomes less and less important when the distance therefrom increases. The reason for this behaviour is evident because when the volume of the bubbles decreases under the influence of the compression, the contribution of the force due to the displaced liquid volume decreases relatively. The figures in parenthesis at FIG. 5 correspond to the volume in $\mu l$ of the bubbles at the pressure under consideration. The shaded horizontal area is intended to remind of the film of the liquid subjected to centrifugation.

Regarding the experimental point of view, the above considerations provided the following observations: between 300 and 600 rpm, the removal of the bubbles from the samples was effected in about 3 to 2 min and very regularly, which was noted by observing under magnification at intervals the liquid subjected to centrifugation (the inspections were done after stopping the rotation). Under rotation velocities of 900 and 1200 rpm, the total homogeneisation was achieved more rapidly but with the difference that a more pronounced effect was observed near the centre for the first seconds of operation.

EXAMPLE 2

A circular mould such as that disclosed on FIGS. 3 and 4 and in conformity with the data of example 1 was used with the exception of the thickness between the plates, the latter being 50 $\mu$. the following reagents were used:

Acrylamide (aqueous solution at 40%)
Methylene bis-acrylamide (ACRYLAMINE-BIS) at 99.9% purity in aqueous solution (origin Bio-RAD). The product was purified by passing over the ion-exchange resin AG 501-X8 (BIO-RAD).
Solution TRIS (TRIZMA), pH of 6.8 and 8.8 (adjusted with HCl). Sterilized in the autoclave.
Sodium dodecyl sulfate (SDS); solution at 20% in $H_2O$; purity 99% (Bio-RAD).
Ammonium persulfate; 10% aqueous solution freshly prepared.
Tetramethylethylenediamine (TEMED); origin BIO-RAD.

In a container adapted for a preliminary degassing under reduced pressure, there were mixed (for a 100 ml of solution) 25 ml of acrylamide solution and 0.33 g of BIS-ACRYLAMIDE. There were added thereafter 37.5 ml of TRIS 1M, pH 8.8 and 36.7 ml of distilled water. After degassing under reduced pressure, there were further added 500 $\mu l$ of SDS (20%), 250 $\mu l$ of persulfate (10%) and 75 $\mu l$ of TEMED. After homogeneisation under agitation, this solution was poured by means of a pipette through the opening 15 of the mould under a rotation of 3000 rpm. The centrifugal force drove immediately the liquid to the periphery where it accumulated, the filling level (which is observed through the upper disc 13) moving progressively in the direction of the centre. A few minutes after the end of the filling of the main portion (the 9/10 of the capacity approximatively) the liquid was homogenized and debubbled under the effect of the centrifugal force and the polymerization causing the setting of the liquid into a solid became effective. After 10 to 15 minutes, the liquid had sufficiently solidified for preventing it from flowing out of the mould in case the rotation motion were stopped.

The gel preparation was thereafter completed by adding to the mould a second liquid comprising, for 100 ml, 7.5 ml of a 40% acrylamide solution and 1.33% of BIS-ACRYLAMIDE, 12;5 ml of TRIS 1M, pH 6.8, 79.2 ml of water and, added after degassing, 500 μl of 20% SDS, 250 μl of 10% persulfate and 75 μl of TEMED. This second portion was injected as indicated above, after the first gel was ready and the whole was allowed to further rotate 15 to 20 min, time within which the second liquid turned into a gel. This second portion constituted then the stacking gel in which, by reason of the presence of pegs 24 during polymerization, there remained recesses in which, after taking apart the device and putting into use the gel film for an electrophoretic analysis, one injects the sample to be fractionated.

It will be noted that many modifications can be added to the present invention; thus one can envisage the possibility of controlling the debubbling process and the centrifugation polymerization by an optical method, for instance by directing against one of the walls of the rotating mould a light signal whose direction is at a non zero angle with the latter and by measuring, either by transmission of by reflection, the modifications produced on this signal by the composition in the mould. Such an inspection can be carried out on a determined annular area if a fixed source is available or following a spiral shaped track if the source (and the detection means) can be moved tangentially. As the signal wave length, the UV range is used preferentially, for which many synthetic resins are transparent. Moreover, the present process is easily suitable to the manufacture of sterilized circular gel films in disposable containers which can be thrown away after use, which limits the hazards of contamination (for instance by viral hepatitis) and enables a standardisation of the analytical methods. Further, one can visualize, in the case of standarized moulds, the incorporation therein of the required buffer for electrophoresis and the preparation of discontinuous gradient gels which result from step polymerization procedures; the manufacture of such special type gels can therefore be automatically controlled by means of the optical detecting means disclosed above.

We claim:

1. Process for moulding gels into films for thin layer electrophoresis and other related techniques of separation by using a mould for thin films in which the principal wall surfaces are transparent and, at least in part, separated one from the other by a distance corresponding to the thickness of the film to be formed and subsequently applying thereto said techniques to separate into components a sample mixture of said components, said process comprising the steps of:
   (a) filling the mould with a gellable mixture to be cast by gravity and subjecting it to a centrifugal gravity field exceeding 3 for effecting efficient debubbling and homogenizing thereof;
   (b) curing said mixture into a gel;
   (c) introducing into the mould in contact with said gel a sample mixture to be subjected to separation;
   (d) contacting the end portions of the gel within the mould with electrodes suitable for electrophoresis; and
   (e) carrying out said electrophoresis operation for a time sufficient for separating the sample mixture into its components.

2. Process according to claim 1, comprising:
   (a) selecting a mould to cast thin layers of polymers essentially consisting of two rigid plates constituting the principal walls of the mould and joined to one another at their periphery by means of assembly for maintaining them essentially parallel and separated from each other by about 5 to 500 μm, these means of assembly which constitute the secondary walls or side walls of the mould being locally interrupted in order to provide, between the plates, an opening through which the mould can be filled with a liquid;
   (b) preparing a liquid composition or solution of a substance that allows formation of a gel;
   (c) rotating the mould in order to subject it to a field of centrifugal forces directed, in general, perpendicular to the opening used for filling and generally parallel to the principal surfaces of the mould and acting from the outside of the mould toward the inside thereof;
   (d) filling the mould with the said liquid by introducing this liquid through the said opening;
   (e) eliminating gas bubbles and other possible faults present in the liquid under the effect of the centrifugal force; and
   (f) curing the liquid into a gel.

3. Process according to claim 2, wherein the curing involves polymerization by irradiation.

4. Process according to claim 2, wherein the main walls of the mould are transparent to an optical signal and, such a signal is applied to the surfaces of said walls at an angle greater than zero degree during stages (d) to (f), the signal reflected or transmitted by the material with which the mould is filled providing a means of control of the operations effected in these stages.

5. Process according to claim 1 wherein the gel is a polyacrylamide gel and said curing comprises the polymerization of a solution of acrylamide monomer.

6. Process according to claim 1, wherein the magnitude of the centrifugal force is 3 to 200 g.

7. Process according to claim 1, wherein the mould is rotated around an axis of rotation, the mould being positioned radially in relation to this axis with the opening turned toward the axis.

8. Process according to claim 1, wherein the mould is filled in stages using several successive fractions of gellable mixture and the curing of each portion is completed before the next portion of mixture is added.

9. Process according to claim 8, wherein after having introduced into the mould a first period of gellable mixture and having transformed this into a gel, a sample to be analyzed is injected into the gel and this first portion of gel is subjected to an electrical field so that the components of the said sample migrate electrophoretically therein: then, when this migration is accomplished, a second portion of gellable mixture is introduced into the mould so that it is in contact with the first portion of gel, the gellable mixture is solidifed and, when this is transformed into a second portion of gel, the latter is subjected to an electrical field so that the components of the sample already fractionated in the first portion of gel will migrate by electrophoresis in this second portion of gel.

10. Process according to claim 1, wherein the centrifugal force applied to the liquid contained in the mould provides a radial variation to its physical chemical properties, said variation following a determined gradient.

11. Process according to claim 6, wherein the sample to be analyzed is mixed with one of said successive fractions.

* * * * *

UNITED STATES PATENT AND TRADEMARK OFFICE
CERTIFICATE OF CORRECTION

PATENT NO. : 4,652,354

DATED : March 24, 1987

INVENTOR(S) : PLACE et al

It is certified that error appears in the above-identified patent and that said Letters Patent is hereby corrected as shown below:

Claim 1, column 11, line 57, change "3" to --3g--.

Signed and Sealed this

Twenty-ninth Day of December, 1987

Attest:

DONALD J. QUIGG

*Attesting Officer*  *Commissioner of Patents and Trademarks*